United States Patent
Yoon et al.

(10) Patent No.: US 11,992,698 B2
(45) Date of Patent: May 28, 2024

(54) LIGHT IRRADIATION DEVICE

(71) Applicant: SEOUL VIOSYS CO., LTD., Gyeonggi-do (KR)

(72) Inventors: Yeong Min Yoon, Gyeonggi-do (KR); Hee Ho Bae, Gyeonggi-do (KR); A Young Lee, Gyeonggi-do (KR); Chung Hoon Lee, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 16/821,024

(22) Filed: Mar. 17, 2020

(65) Prior Publication Data
US 2020/0298016 A1    Sep. 24, 2020

Related U.S. Application Data

(60) Provisional application No. 62/820,493, filed on Mar. 19, 2019.

(51) Int. Cl.
*A61N 5/06* (2006.01)
*H05B 47/155* (2020.01)
*H05B 47/16* (2020.01)

(52) U.S. Cl.
CPC ......... *A61N 5/0624* (2013.01); *A61N 5/0616* (2013.01); *H05B 47/155* (2020.01);
(Continued)

(58) Field of Classification Search
CPC .......... A61N 2005/0642; A61N 5/0616; A61N 2005/0659; A61N 2005/0629; H05B 47/155
See application file for complete search history.

(56) References Cited

U.S. PATENT DOCUMENTS

2004/0122492 A1    6/2004    Harth
2009/0177253 A1    7/2009    Darm et al.
(Continued)

FOREIGN PATENT DOCUMENTS

EP    2383017 A1    11/2011
JP    2007-514459 A    6/2007
(Continued)

OTHER PUBLICATIONS

Ash C, Dubec M, Donne K, Bashford T. Effect of wavelength and beam width on penetration in light-tissue interaction using computational methods. Lasers Med Sci. 2017;32(8):1909-1918. doi:10.1007/s10103-017-2317-4 (Year: 2017).*

(Continued)

*Primary Examiner* — Carl H Layno
*Assistant Examiner* — Aya Ziad Bakkar
(74) *Attorney, Agent, or Firm* — Perkins Coie LLP

(57) ABSTRACT

A light irradiation device includes a light source unit emitting a light to a wounded are of a skin and a controller controlling the light source unit. The light source unit includes a substrate, at least one first light source disposed on the substrate and emitting a first light in a blue wavelength band, and at least one second light source disposed on the substrate and emitting a second light in a red wavelength band to a near-infrared wavelength band. The first and second lights have different skin penetration depths from each other depending on a wavelength.

20 Claims, 9 Drawing Sheets

(52) U.S. Cl.
CPC ...... *H05B 47/16* (2020.01); *A61N 2005/0626* (2013.01); *A61N 2005/0629* (2013.01); *A61N 2005/0645* (2013.01); *A61N 2005/0659* (2013.01); *A61N 2005/0663* (2013.01)

(56) References Cited

U.S. PATENT DOCUMENTS

| | | | |
|---|---|---|---|
| 2014/0194955 A1* | 7/2014 | Povolosky | A61N 2/002 607/89 |
| 2014/0303547 A1 | 10/2014 | Loupis et al. | |
| 2016/0016001 A1* | 1/2016 | Loupis | A61N 5/0616 604/20 |
| 2017/0246474 A1 | 8/2017 | Schanze | |

FOREIGN PATENT DOCUMENTS

| | | |
|---|---|---|
| JP | 2011-509122 A | 3/2011 |
| JP | 2016-511672 A | 4/2016 |
| KR | 20110054413 A * | 5/2011 |
| KR | 1020120069588 A | 6/2012 |
| KR | 1020150032994 A | 4/2015 |
| KR | 101561448 B1 * | 10/2015 |
| KR | 1020150143456 A | 12/2015 |
| WO | 2005030317 A2 | 4/2005 |
| WO | 2013070946 A2 | 5/2013 |
| WO | 2018134298 A1 | 7/2018 |

OTHER PUBLICATIONS

International Search Report for International Application No. PCT/KR2020/003692, dated Jun. 17, 2020, 2 pages.
European Search Report from corresponding European Patent Application No. 20773884.0, dated Nov. 7, 2022 (7 pages).
Office Action from corresponding Japanese Patent Application No. 2021-556330, dated Nov. 21, 2023 (16 pages).

* cited by examiner

LIGHT IRRADIATION DEVICE

CROSS-REFERENCE TO RELATED APPLICATION(S)

This application is a non-provisional application of Provisional Application No. 62/820,490 filed Mar. 19, 2019, the content of which is incorporated herein by reference in their entirety.

TECHNICAL FIELD

The present disclosure relates to a light irradiation device. More particularly, the present disclosure relates to a light irradiation device used for treatment.

BACKGROUND

Recently, various treatment devices using ultraviolet light have been under development. In general, ultraviolet light is known to have a sterilization effect, and conventional ultraviolet-light treatment devices are utilized by using conventional UV lamps and operating the UV lamps near a skin to irradiate the UV light to an area requiring treatment.

However, besides the sterilization effect, the ultraviolet light irradiation causes harmful effects such as skin aging and cancer. Accordingly, there is a demand for a method of obtaining sterilization and treatment effects with ultraviolet light irradiation in a safe manner for treatment purpose.

SUMMARY

The present disclosure provides a light irradiation device having high sterilization and skin regeneration effects while minimizing adverse effects on a human body.

Embodiments of the present disclosure provide a light irradiation device including a light source unit emitting a light to a wounded skin and a controller controlling the light source unit. The light source unit includes a substrate, at least one first light source disposed on the substrate and emitting a first light in a blue wavelength band, and at least one second light source disposed on the substrate and emitting a second light in a red to a near-infrared wavelength band. The first and second lights have different skin penetration depths from each other depending on a wavelength, and a difference in the skin penetration depth between the first light and the second light is equal to or greater than about 1.8 mm.

In some embodiments, the first light has the skin penetration depth equal to or greater than about 1.0 mm. Additionally, or alternatively, the second light has the skin penetration depth equal to or greater than about 4.3 mm. For example, the first light has a wavelength band of about 370 nm to about 500 nm. As another example, the second light has a wavelength band of about 610 nm to about 940 nm.

In some embodiments, he first light and the second light are substantially simultaneously irradiated for a predetermined time. In other embodiments, the first light is irradiated for a first time, and the second light is irradiated for a second time longer than the first time. The second light starts to be irradiated before the irradiation of the first light is completed, and at least a portion of the first time overlaps at least a portion of the second time.

In some embodiments, the second light is irradiated continuously. The first light is irradiated discontinuously. At least one of the first light and the second light is periodically irradiated.

The light irradiation device according to embodiments of the present disclosure is used for treatment. An irradiation area of the first light on the skin is smaller than an irradiation area of the second light on the skin.

The substrate faces the skin and includes a first region in which the first light source is disposed and a second region in which the second light source is disposed, and the second region surrounds the first region. A surface corresponding to the first region is disposed to be more spaced apart from the skin than a surface corresponding to the second region is.

According to the above, the light irradiation device having the high sterilization and the skin regeneration effects while minimizing the adverse effects on the human body may be provided.

BRIEF DESCRIPTION OF THE DRAWINGS

The above and other advantages of the present disclosure will become readily apparent by reference to the following detailed description when considered in conjunction with the accompanying drawings wherein:

FIG. 3A illustrates a first method of driving the light irradiation device according to embodiments of the present disclosure.

FIG. 3B illustrates a second method of driving the light irradiation device according to embodiments of the present disclosure.

FIG. 3C illustrates a third method of driving the light irradiation device according to embodiments of the present disclosure.

FIG. 3D illustrates a fourth method of driving the light irradiation device according to embodiments of the present disclosure.

FIG. 3E illustrates a fifth method of driving the light irradiation device according to embodiments of the present disclosure. and FIG. 3F illustrates a sixth method of driving the light irradiation device according to embodiments of the present disclosure;

FIGS. 5A to 54D are conceptual views showing the operation mechanism of FIG. 4 sequentially in the order of occurrence, where:

FIG. 5A illustrates an exemplary view of damaged epidermis and dermis in a wounded site of skin;

FIG. 8 is a graph showing sterilization effects in accordance with irradiation conditions when a light is irradiated to a wound using a conventional light irradiation device and a light irradiation device according to an exemplary embodiment of the present disclosure; and FIG. 9 is a graph showing a recovery period of the wound in accordance with the irradiation conditions when the light is irradiated to the wound using a conventional light irradiation device and a light irradiation device according to an exemplary embodiment of the present disclosure.

DETAILED DESCRIPTION OF EMBODIMENTS

Figure 1:
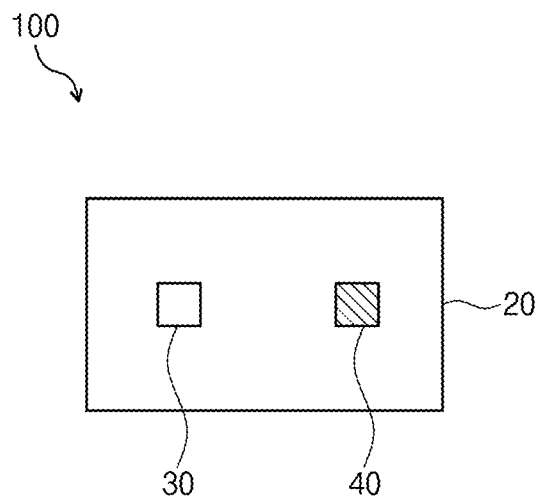
FIG. 1 is a plan view showing a light irradiation device according to an exemplary embodiment of the present disclosure.

The present disclosure may be variously modified and realized in many different forms, and thus specific embodiments will be exemplified in the drawings and described in detail hereinbelow. However, the present disclosure should not be limited to the specific disclosed forms, and be construed to include all modifications, equivalents; or replacements included in the spirit and scope of the present disclosure.

Hereinafter, exemplary embodiments of the present disclosure will be explained in detail with reference to the accompanying drawings.

FIG. 1 is a plan view showing a light source unit 10 of an irradiation device according to an exemplary embodiment of the present disclosure. Referring to FIG. 1, the light source unit 10 according to the exemplary embodiment of the present disclosure emits a light to a selected area of a skin such as a wounded area of the skin.

The light source unit 10 includes a substrate 20, at least one first light source 30 disposed on the substrate 20 and emitting a first light in a blue wavelength band, and at least one second light source 40 disposed on the substrate 20 and emitting a second light in red to an infrared wavelength band.

The substrate 20 should not be particularly limited as long as the first and second light sources 30 and 40 are available to be mounted thereon. The substrate 20 may be provided in various forms. In some embodiments, the substrate 20 may be provided with wires to supply a power to the first and second light sources 30 and 40. The substrate 20 may include, for example, a metal substrate or a printed circuit board, on which the wires are formed.

The first light source 30 may emit the first light in the blue wavelength band of a visible light wavelength band. The first light may correspond to a light with a wavelength band from about 370 nm to about 500 nm. In some embodiments, the first light may be a light with a wavelength band from about 385 nm to about 435 nm. More particularly, the first light may be a light with a wavelength band from about 400 nm to about 420 nm, preferably, about 410 nm. In other embodiments, the wavelength band of the first light is not limited thereto.

The first light has a higher penetration force into an area of a skin than an ultraviolet light and corresponds to a wavelength band that is harmless to the human body. The first light corresponds to an absorption wavelength of porphyrins present in pathogens such as bacteria. When the first light is applied to the bacteria, the porphyrins in the bacteria absorb the first light, and reactive oxygen species (ROS) are produced in cells of the bacteria by the energy of the first light. The reactive oxygen species are accumulated in the cells of the bacteria and oxidize cell walls of bacteria, and as a result, that bacteria are killed. That is, the pathogens may be killed by inducing an oxidative stress in the pathogens by the ROS.

The second light source 40 emits the second light in a red visible light to a near-infrared wavelength band. The second light may correspond to a light in the wavelength band from about 610 nm to about 940 nm. In the exemplary embodiment of the present disclosure, the second light may be a light with a red visible light wavelength band, for example, from about 610 nm to about 750 nm, or an infrared light wavelength band, for example, from about 750 nm to about 940 nm. As another example, the second light according to the exemplary embodiment of the present disclosure may be a light with the infrared light wavelength band of about 830 nm, about 850 nm, or about 890 nm.

The second light is applied to a certain area of a skin to dilate blood vessels and promote a blood circulation. That is, the second light improves a blood flow, and as a result, immune response is promoted.

In more detail, the red visible light to the near-infrared light acts on a certain area of a skin to be treated and stimulates mitochondria in cells to produce adenosine triphosphate (ATP), the reactive oxygen species (ROS), and/or nitrogen oxide (NO). The ATP, ROS, and/or NO act on a wounded site to promote wound healing. The ATP and ROS induce the expression of genes involved in inflammatory response that is an immune response required for wound healing and genes needed for cell growth. In addition, the ROS and/or NO have an ability to sterilize pathogens such as bacteria that penetrate into the wounded site. Accordingly, the inflammatory response and the cell growth are induced in damaged tissue areas, resulting in wound healing. The NO promotes migration of immune cells and increases supply of oxygen and nutrients to accelerate tissue healing processes. In addition, the NO expands capillaries in surrounding tissues and induces formation of new capillaries.

In some embodiments, when the first and second lights are irradiated substantially simultaneously, or alternatively, the first and second lights are irradiated not simultaneously, i.e., at different timings, but sequentially in a predetermined time, a higher wound healing effect may be achieved than when each of the first and second lights is irradiated alone.

According to the embodiments of the present disclosure, as the pathogens in the wounded site are sterilized by the first light and an immune mechanism is promoted by the second light, the wound may be efficiently healed. When a certain area of the skin is injured, not only the sterilization of the pathogens but also treatment of infected cells are required for the complete wound healing. Although the first light is effective to sterilize the pathogens, the function of inducing the immune mechanism in the skin of the wounded site is not large when only the first light is used. In particular, in the case of deep or complex wounds, a penetration depth of the light varies depending on the wavelength of the light, and the sterilization effect is lowered. As a result, unsterilized pathogens in the wound may be re-proliferated. When unsterilized pathogens are re-proliferated, the wound healing is delayed. The second light promotes the immune mechanism of the skin before unsterilized pathogens are re-proliferated, and thus, the wound may be effectively healed in a relatively short time.

In the present embodiment, the pathogens refer to microorganisms that cause diseases, such as viruses, bacteria, fungi, protozoa, and hosts. In general, anything that causes diseases may be included in the pathogens.

The light irradiation device 100 according to the exemplary embodiment of the present disclosure may be used to heal the wound that requires treatment. For example, the light irradiation device 100 may be used not only for simple wounds but also may be used for chronic diseases, such as a normal ulcer, a pressure ulcer, or an ischemic ulcer due to diabetes. In addition, the light irradiation device 100 may be used for a variety of wounds, e.g., a surgical site infection due to surgery, a laceration in which tissues are torn apart, an incised wound in which skin and tissues are cut with a sharp instrument, a punctured wound caused by a sharp object such as a knife or spear, etc.

According to the exemplary embodiment of the present disclosure, the wounded site may be sterilized without using the ultraviolet light. Although the ultraviolet light may reduce the amount of pathogens, the ultraviolet light induces mutations in DNA of skin cells. Therefore, overexposure to the ultraviolet light may cause a skin cancer, and there is a need to control a dose of the ultraviolet light. In the case of the ultraviolet light, since the wavelength is very short and the penetration into the skin is low, the sterilization of pathogens in wounds outside the skin may be partially possible. However, in the case of wounds with a predetermined depth or more, it is impossible to sterilize the pathogens inside. This is because there is a difference in penetration depth into the wounded skin depending on a wavelength of external light, and the shorter the wavelength is, the thinner the penetration depth may be in the skin.

According to the exemplary embodiment of the present disclosure, as a combination of the first light and the second light having different penetration depths is used, it is possible to enhance the healing effect on the wounded site as a whole rather than a specific position. This will be described in detail later.

Figure 2:
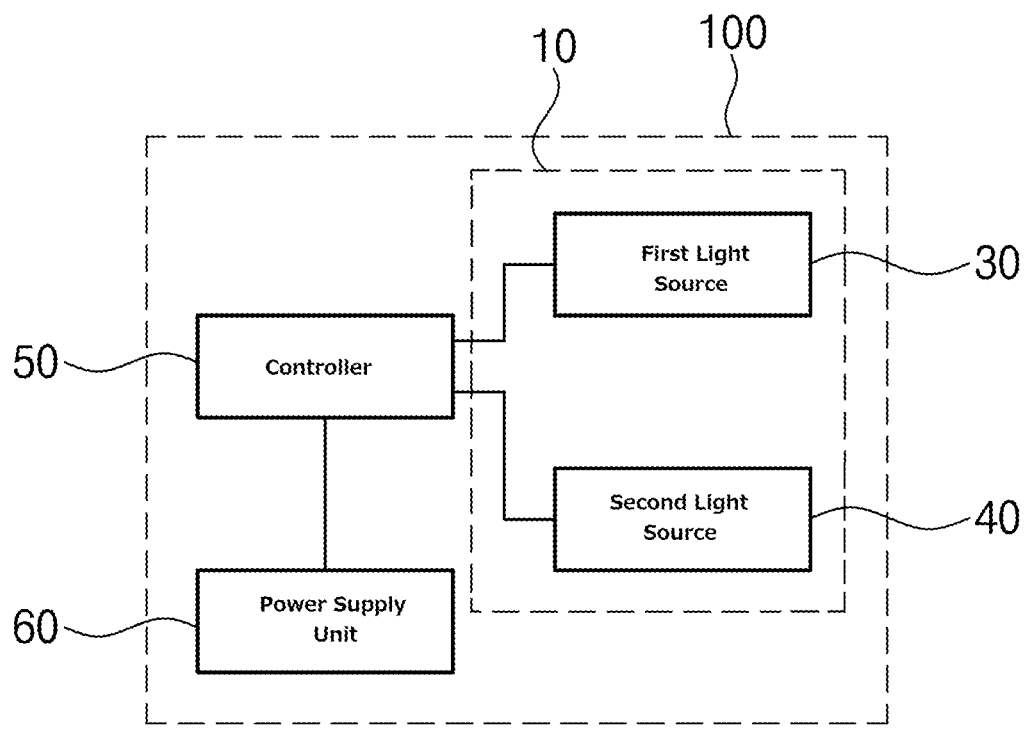
FIG. 2 is a block diagram showing a light irradiation device according to an exemplary embodiment of the present disclosure.

FIG. 2 is a block diagram showing the light irradiation device 100 according to an exemplary embodiment of the present disclosure. Referring to FIG. 2, the light irradiation device 100 according to the exemplary embodiment of the present disclosure may include the light source unit 10 having the first light source 30 emitting the first light and the second light source 40 emitting the second light, a controller 50 controlling the first and second light sources 30 and 40 such that the second light source 40 emits the second light after the first light source 30 emits the first light, and a power supply unit 60 supplying a power to the first and second light sources 30 and 40.

As described above, the first and second light sources 30 and 40 may emit the first light with the blue wavelength band and the second light with the red visible light to the near-infrared wavelength band, respectively.

The controller 50 may control whether to emit the light from the first and second light sources 30 and 40, an amount of the light, an intensity of the light, emission time, and the like. The power supply unit 60 may be electrically connected to the first and second light sources 30 and 40 and the controller 50 and may supply the power to the first and second light sources 30 and 40 and the controller 50. In FIG. 2, the power supply unit 60 supplies the power to the first and second light sources 30 and 40 via the controller 50; however, it should not be limited thereto or thereby. That is, the power supply unit 60 may be connected directly to the first and second light sources 30 and 40 to supply the power to the first and second light sources 30 and 40.

In some embodiments, the light irradiation device 100 may further include an optical unit that selectively focuses or disperses the lights emitted from the first and second light sources 30 and 40. The optical unit may focus the lights generated by the first and second light sources 30 and 40 into a narrow range or a wide range as necessary. The optical unit may focus or disperse the light in a uniform or non-uniform form depending on a position to which the light is irradiated. The optical unit may include at least one lens as needed, and the lens may perform various functions, such as focusing, dispersing, uniformizing, and non-uniformizing the lights from the first and second light sources 30 and 40.

For example, in the case where the light is irradiated to a small area using the light irradiation device 100 according to the exemplary embodiment of the present disclosure, a lens for focusing the light may be used in the first and second light sources 30 and 40. On the contrary, in the case where the light is irradiated to a wide area, for example, a whole room, using the light irradiation device 100 according to the exemplary embodiment of the present disclosure, a lens for dispersing the light may be used. For example, additional lenses may be added to the first light source 30 and the second light source 40 to allow the first light source 30 to irradiate the light to a relatively small area directly corresponding to the wounded site and to allow the second light source 40 to irradiate the light to a relatively wide area corresponding to the wounded site and surrounding area adjacent to the wound.

In the present exemplary embodiment, the controller 50 individually drives the first light source 30, the second light source 40, or both. That is, the first and second light sources 30 and 40 may be substantially simultaneously turned on/off, or the first and second light sources 30 and 40 may be individually turned on/off. In addition, the intensity of the lights emitted from the first light source 30 and the second light source 40, i.e., the intensity of the first and second lights, may be simultaneously or individually controlled. However, the controller 50 drives the first light source 30 and the second light source 40 such that a process of applying the first light and the second light within a predetermined range of time is included when driving the first light source 30 and the second light source 40.

According to the exemplary embodiment of the present disclosure, the first light may be applied to an object to be sterilized during a predetermined time, and the second light may be irradiated simultaneously with the first light or after the first light is irradiated. Accordingly, in addition to the effect obtained from the second light, it is possible to prevent the re-proliferation of the unsterilized pathogens again as much as possible after the irradiation of the first light. As a result, an improved wound-healing effect may be obtained compared with irradiation of the first light alone. In the exemplary embodiment of the present disclosure, a synergy effect of the wound healing may be obtained through the irradiation of both the first light and the second light. When turning on/off the first light source 30 and the second light source 40 to obtain the above-described effects, various implementations are available. For instance, as to the first light source 30 and the second light source 40, a method of emitting lights simultaneously, a method of continuously emitting lights, a method of sequentially decreasing or increasing the intensity of lights, a flickering method, or a mixed method may be employed.

FIGS. 3A to 3F illustrate various implementations of methods for driving the light irradiation device according to an exemplary embodiment of the present disclosure to show on/off time of the first and second light sources. In FIGS. 3A to 3F, the first and second lights of the light irradiation device according to the exemplary embodiment of the present disclosure are respectively referred to as "L1" and "L2", and a time lapse is represented by "T".

Figure 3A:
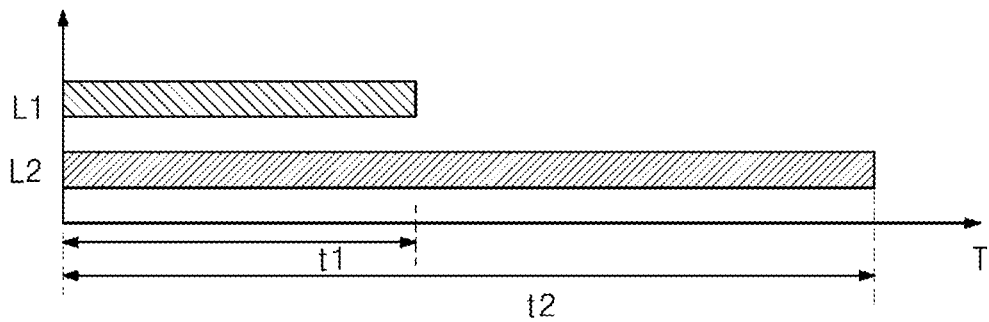
FIGS. 3A to 3F are graphs showing a method of driving a light irradiation device according to an exemplary embodiment of the present disclosure to show on/off time of first and second light sources, where.

FIG. 3A illustrates a first method of driving the light irradiation device according to embodiments of the present disclosure. Referring to FIG. 3A, the first light source is turned on for a first time t1 to irradiate the first light L1, and the second light source is turned on for a second time t2 to irradiate the second light L2. In the present exemplary embodiment, the second time t2 for which the second light L2 is irradiated may be longer than the first time t1 for which the first light L1 is irradiated. Since the first light L1 is to sterilize the wounded site, the first light L1 may be irradiated until a time point where the wounded site is sufficiently sterilized. The second light L2, which is the light with the red to the near-infrared wavelength band, may be irradiated for a longer time while the wound is healed to promote the immune response.

The irradiation time and the irradiation amount of the first and second lights L1 and L2 respectively emitted from the first and second light sources may be changed in various ways. In the exemplary embodiment of the present disclosure, the first light L1 and the second light L2 may be simultaneously irradiated, and as described above and shown in FIG. 3A, the irradiation of the second light L2 may be performed for a longer time than the irradiation of the first light L1. In the case of the first light L1, a total dose may be set in various ranges within a range that is harmless to the human body depending on the object to be sterilized. In the case of the second light L2, a total dose may be set within a limit that is harmless to the human body, for example, within a range where there is no risk of low temperature burn.

Figure 3B:
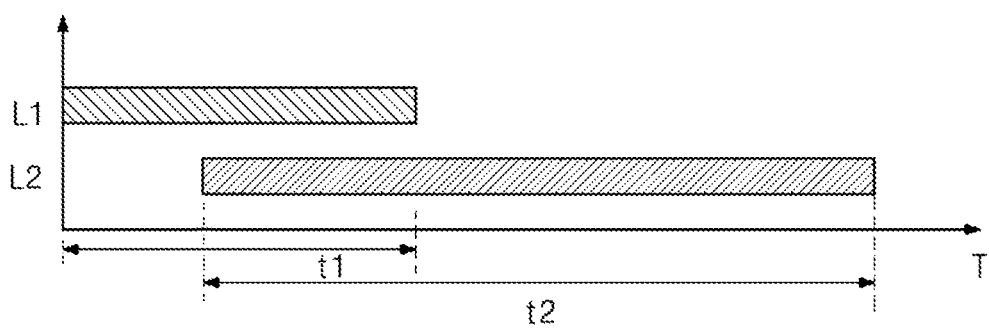

In the present exemplary embodiment, the application frequency and the timing of application of the first light L1 and the second light L2 may vary. FIG. 3B illustrates a second method of driving the light irradiation device according to embodiments of the present disclosure. As one example, referring to FIG. 3B, when the first light L1 and the second light L2 are applied, both the first light L1 and the second light L2 may be applied continuously.

Figure 3C:
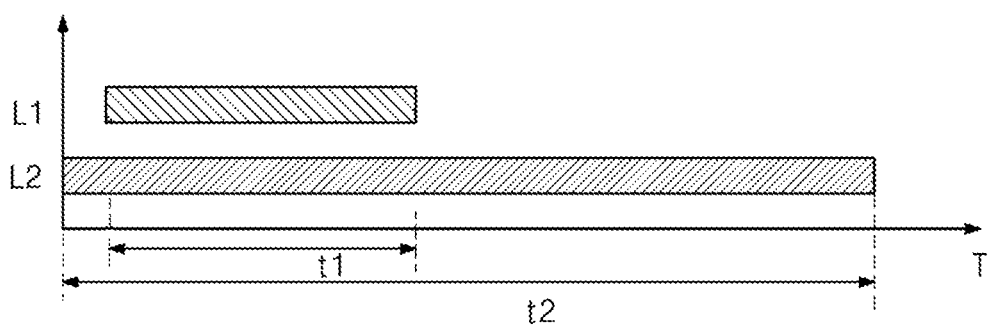

FIG. 3C illustrates a third method of driving the light irradiation device according to embodiments of the present disclosure. As another example, referring to FIG. 3C, the second light L2 may not be provided continuously and provided in a discontinuous manner with the first light L1, while the first light L1 is continuously applied without interruption to the object to be sterilized.

Figure 3D:
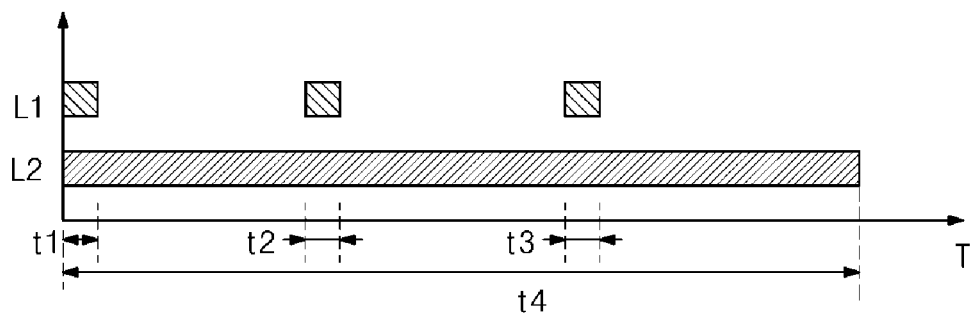
Figure 3E:
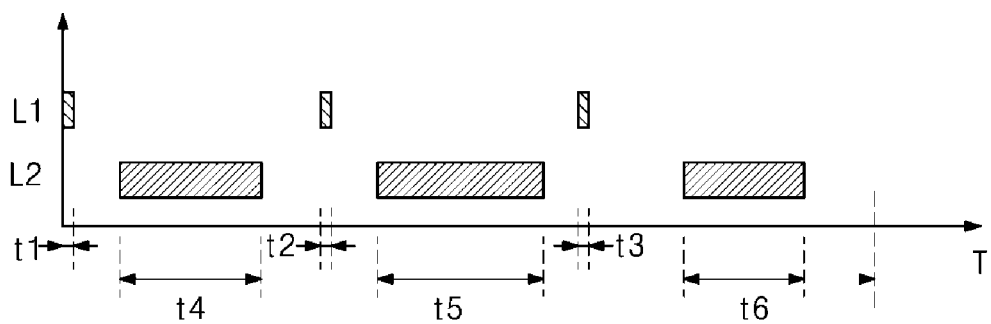

Referring to FIGS. 3A to 3C, the irradiation of the first light L1 and the second light L2 may be performed once for a predetermined time period. However, as shown in FIGS. 3D and 3E, the first light L1 or the second light L2 may be irradiated a plurality of times at intervals. FIG. 3D illustrates a fourth method of driving the light irradiation device according to embodiments of the present disclosure. FIG. 3E illustrates a fifth method of driving the light irradiation device according to embodiments of the present disclosure.

For example, referring to FIGS. 3D and 3E, the first light L1 may be applied three times during the first time t1, the second time t2, and a third time t3, and the second light L2 may be applied during a fourth time t4. The first light L1 may be applied periodically at regular intervals or aperiodically at irregular intervals.

Referring to FIG. 3B, at least a portion of the irradiation time of the first light L1 may overlap a portion of the irradiation time of the second light L2. As shown in FIG. 3B, although the irradiation of the first light L1 does not start together with the irradiation of the second light L2 at the same time point, the irradiation of the second light L2 may start before the application of the first light L1 is completed.

Figure 3F:
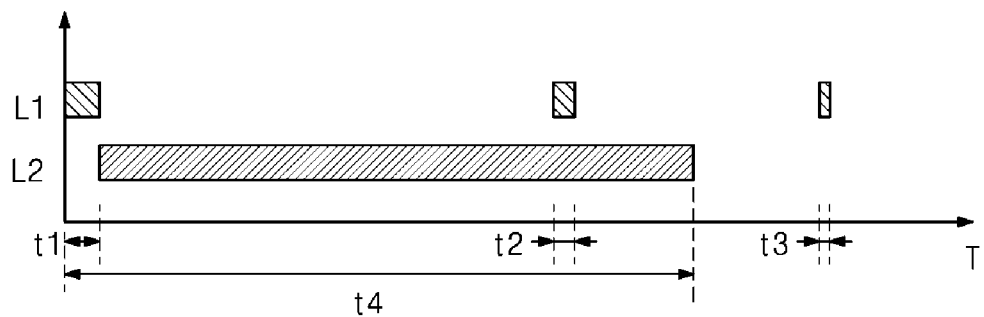

In the exemplary embodiment of the present disclosure, the time point at which the first light L1 starts to be applied may be different from the time point at which the second light L2 starts to be applied. For example, the first light L1 and the second light L2 may start to be applied at the same time point as shown in FIGS. 3A and 3D, or may start to be applied at different time points from each other as shown in FIGS. 3B, 3C, 3E, and 3F. FIG. 3F illustrates a sixth method of driving the light irradiation device according to embodiments of the present disclosure. In the case of FIG. 3C, the application of the second light L2 starts before the application of the first light L1, and in the case of FIGS. 3B, 3E, and 3F, the application of the first light L1 starts before the application of the second light L2.

Referring to FIG. 3E, both the first light L1 and the second light L2 may be applied three times. In this case, the first light L1 may be applied during the first time t1, the second time t2, and the third time t3, and the second light L2 may be applied during the fourth time t4, a fifth time t5, and a sixth time t6. A repetition cycle and the number of repetitions of irradiation of the first and/or second lights L1 and L2 may vary depending on types of objects to be cured and total amount of light.

In the embodiments of the present disclosure as discussed above, the first light L1 may be irradiated to overlap with the time during which the second light L2 is applied, or alternatively may not overlap. For example, referring to FIGS. 3A and 3D, during the time that the second light L2 is applied, the first light L1 may be irradiated to overlap the second light L2. Referring to FIG. 3E, the time that the first light L1 is applied does not overlap the time that the second light L2 is applied, and the first and second lights L1 and L2 may be applied during different times from each other. Referring to FIG. 3F, the time that the first light L1 is applied may or may not overlap the time that the second light L2 is applied. In the case of FIG. 3F, the first and third times t1 and t3 during which the first light L1 is applied do not overlap with the fourth time t4 during which the second light L2 is applied, and the second time t2 during which the first light L1 is applied overlaps the fourth time t4 during which the second light L2 is applied.

In the exemplary embodiment of the present disclosure, in the case where the first light L1 and/or the second light L2 are applied several times, the time during which the irradiation of the first light L1 is maintained and the time during which the irradiation of the second light L2 is maintained may be the same as each other or different from each other. For example, as shown in FIGS. 3D and 3E, the first time t1, the second time t2, and the third time t3 each during which the first light L1 is applied may be the same value. On the other hand, as shown in FIG. 3F, the first time t1, the second time t2, and the third time t3 each during which the first light L1 is applied may be different values. This is the same with the second light L2.

In the exemplary embodiment of the present disclosure, the second light L2 may start to be applied after the irradiation of the first light L1 is completed, however, as shown in FIGS. 3B, 3E, and 3F, the second light L2 may start to be applied while the irradiation of the first light L1 is in progress, or at the moment that the irradiation of the first light L1 is completed. This is to prevent the re-proliferation of unsterilized bacteria as much as possible after the sterilization of the pathogens by the first light L1. In some embodiments of the present disclosure, when the irradiation of the second light L2 starts after the irradiation of the first light L1 is completed as shown in FIG. 3E, the second light L2 is required to be applied as soon as possible after the irradiation of the first light L1 is completed for the efficient curing.

As described above, the light irradiation device according to the exemplary embodiment of the present disclosure irradiates the first light L1 and the second light L2 using the first light source and the second light source to treat the wound, and the first light L1 and the second light L2 have different penetration depths from each other when being applied to area(s) of the skin. Hereinafter, an operation mechanism of the light irradiation device according to the exemplary embodiment of the present disclosure will be described.

Figure 4:
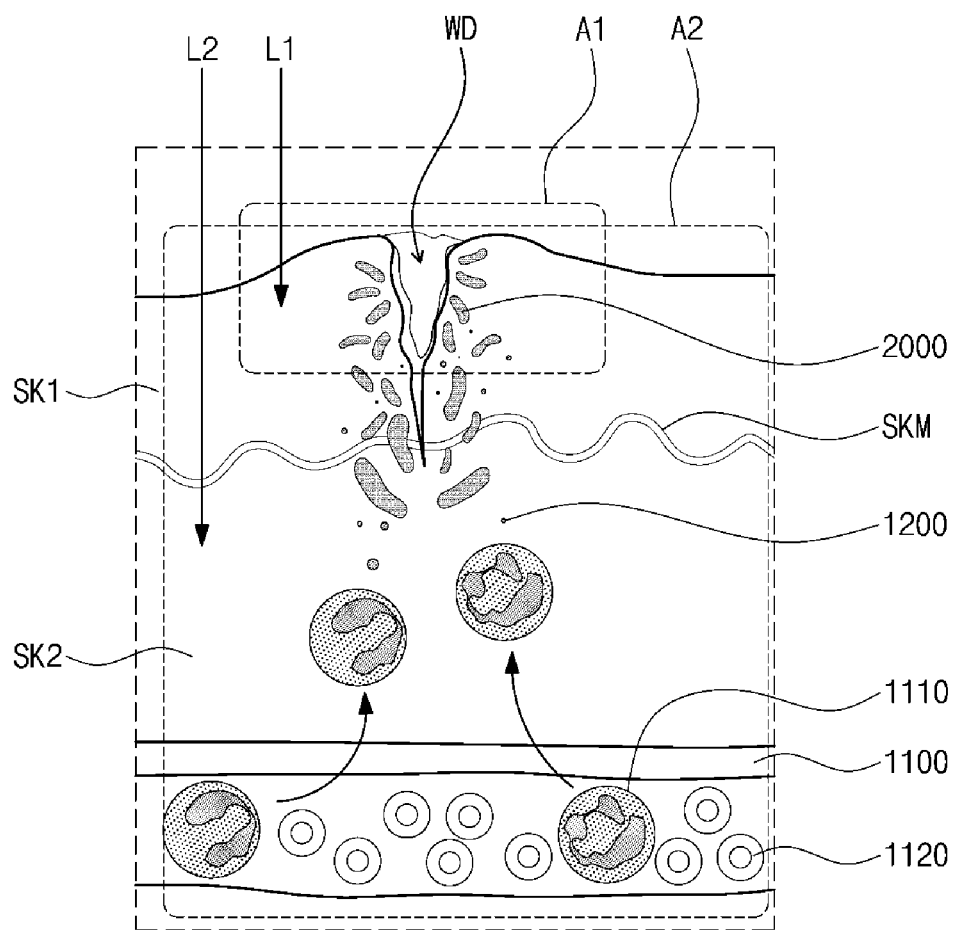
FIG. 4 is a view showing an operation mechanism of a light irradiation device according to an exemplary embodiment of the present disclosure.

FIG. 4 is a view showing the operation mechanism of the light irradiation device according to an exemplary embodiment of the present disclosure, and FIGS. 5A to 5D are conceptual views showing the operation mechanism of FIG. 4 sequentially in the order of occurrence. In FIG. 4, a first light and a second light of the light irradiation device according to the exemplary embodiment of the present disclosure are indicated by "L1" and "L2", respectively.

In some embodiments of the present disclosure, referring to FIG. 4, the lights emitted from the first and second light sources of the light irradiation device are applied to a certain area of the skin. The skin protects the human body from external pathogens 2000 and includes an epidermis SK1, which is a stratified squamous epithelium, a dermis SK2, which is a tight connective tissue, and a subcutaneous tissue (not shown), which is a loose connective tissue. For the convenience of explanation, FIG. 4 shows mainly the epidermis SK1, the dermis SK2, and a blood vessel 1100 in the dermis SK2. The epidermis SK1 provides a waterproofing function and acts as a barrier to infection. The dermis SK2 is a layer of skin beneath the epidermis SK1 that consists of the connective tissue and cushions the body from stress and strain. The dermis SK2 is tightly connected to the epidermis SK1 through a basement membrane SKM. The epidermis SK1 contains no blood vessel 1100 and the dermis SK2 contains the blood vessel 1100.

When a wound occurs in the skin, the pathogens 2000 may penetrate the body through the wound. The human body responds to the pathogens 2000 penetrated into tissues in the skin, and as a result, a cytokine 1200 is secreted by immune cells. The cytokine 1200 secreted from one cell affects other cells or the secreting cell itself. For example, the cytokine 1200 may induce proliferation of macrophages or may promote differentiation of the secreting cell itself. When the first light L1 and the second light L2 are irradiated by the light irradiation device according to the exemplary embodiment of the present disclosure in the above-described process, the wound may heal relatively quickly. This will be described with reference to drawings.

Figure 5A:
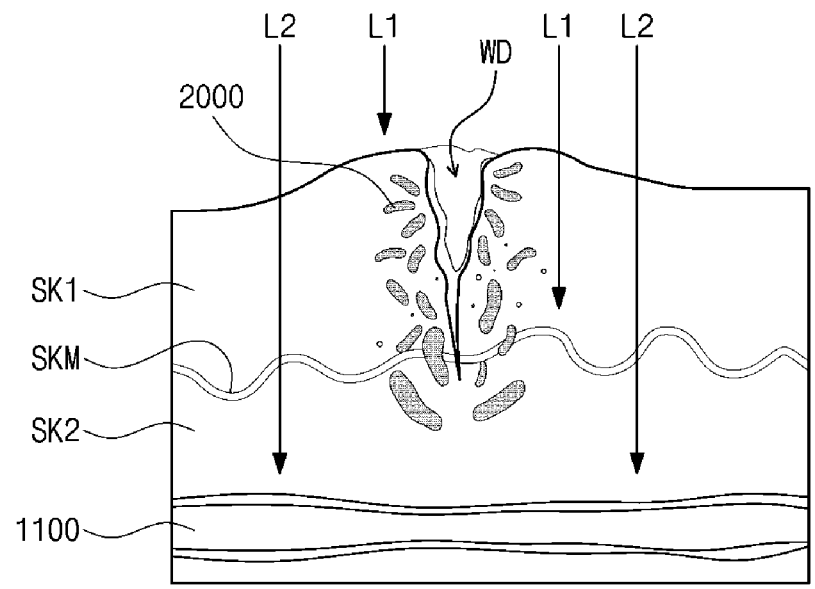

Referring to FIGS. 4 and 5A, when the wound occurs in the skin, the epidermis SK1 may be damaged, or the epidermis SK1 and the dermis SK2 may be damaged depending on the extent of the wound. FIG. 4 shows the wound in which the epidermis SK1 and a portion of the dermis SK2 are damaged.

In the case where the epidermis SK1 and the portion of the dermis SK2 are damaged, the pathogens 2000 penetrate into the human body through the damaged portions of the epidermis SK1 and the dermis SK2. The pathogens 2000 may be most commonly present around the wound and may partially penetrate into the tissue in the skin.

According to the exemplary embodiment of the present disclosure, the first light L1 and the second light L2 may be provided to the wounded site.

As described above, the first light L1 and the second light L2 may have different wavelength bands from each other. The first light L1 has a relatively short wavelength, and the second light L2 has a relatively long wavelength. The first light L1 and the second light L2 have different penetration distances into the skin depending on their wavelengths. When a maximum penetration depth in the skin of the first light L1 is referred to as a first distance and a maximum penetration depth in the skin of the second light L2 is referred to as a second distance, the second distance is larger than the first distance. In FIG. 4, an area into which the first light L1 may penetrate and an area into which the second light L2 may penetrate are indicated by a first zone A1 and a second zone A2, respectively. The first zone A1 may be in the epidermis SK1, and the second zone A2 may be positioned in a corresponding area from the epidermis SK1 to the dermis SK2.

In more detail, the first light L1 may have the wavelength from about 370 nm to about 500 nm and more particularly, in the wavelength band from about 370 nm to about 420 nm. The second light L2 may have the wavelength from about 610 nm to about 940 nm and more particularly, in the wavelength band from about 610 nm to about 750 nm or from about 750 nm to about 940 nm. The first light L1 may penetrate into the epidermis SK1 of the skin, and the second light L2 may penetrate into the dermis SK2 of the skin as well as the epidermis SK1. In more detail, the first light L1 may have the skin penetration depth of about 1 mm or more, and the second light L2 may have the skin penetration depth of about 4.3 mm or more. In addition, the maximum penetration depth in the skin of the first light L1 may be about 2.5 mm, and thus, a difference in the skin penetration depth between the first light L1 and the second light L2 may be equal to or greater than about 1.8 mm.

The penetration depth into the skin according to the wavelength of each light is as shown in Table 1 below.

TABLE 1

| Wavelength (nm) | Depth (mm) |
| --- | --- |
| 300 | 0.5 |
| 350 | 0.8 |
| 400 | 1 |
| 450 | 1.5 |
| 500 | 2.5 |
| 550 | 3 |
| 600 | 4.3 |
| 650 | 4.8 |
| 700 | 5.2 |
| 750 | 5.4 |

The first light L1 acts on the epidermis SK1 of the wounded site to sterilize the pathogens 2000 present around the wound or penetrated into the skin. Since the first light L1 has the relatively short wavelength, it may be difficult to sterilize all pathogens 2000 in the dermis SK2 when the wound reaches or affects the dermis SK2.

Figure 5B:
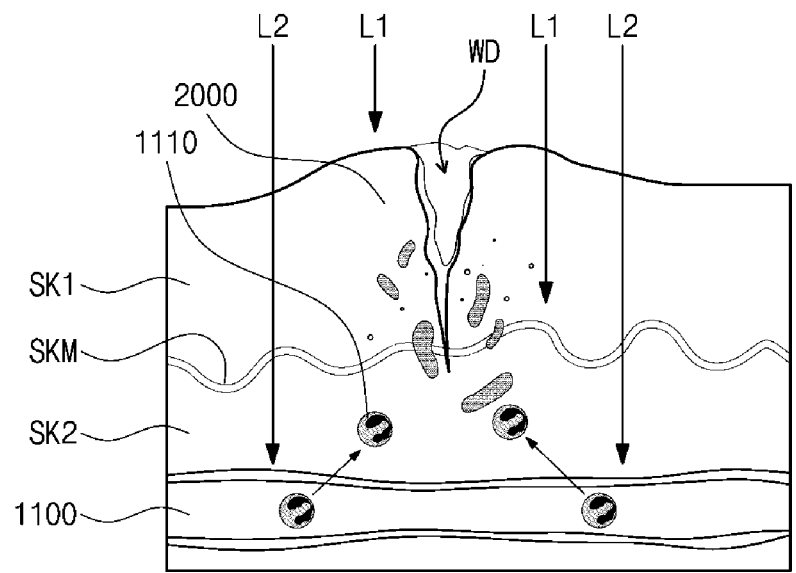
FIG. 5B illustrates an exemplary view of pathogens in the dermis in the wounded site of skin as shown FIG. 5A.

Referring to FIGS. 4 and 5B, most of the pathogens 2000 in the epidermis SK1 may be sterilized and removed by the first light L1, but some pathogens 2000 in the dermis SK2 may remain. The immune system in the skin tissue confirms the infection by recognizing the pathogens 2000 remaining in the dermis SK2 and releases an immune-active substance (e.g., the cytokine 1200). Through the immune response, the blood vessel 1100 of the wounded site are expanded, and cells for immunity, such as leukocytes 1110 and macrophages, migrate to the wounded site to activate the inflammatory mechanism. The second light L2 penetrates into the dermis SK2 through the epidermis SK1 and acts on the dermis SK2, and thus, the blood vessel 1100 in the wounded site is more expanded. The second light L2 also promotes the migration of immune cells (e.g., leukocytes 1110) from the expanded blood vessel 1100. The immune cells migrate to the wounded site, and ingest and remove the infiltrated foreign material, i.e., pathogens 2000. As the immune mechanism in the dermis SK2 is activated by the second light L2, the pathogens 2000 unsterilized by the first light L1 may be effectively removed. In FIG. 4, a reference numeral "1120" denotes erythrocyte.

Figure 5C:
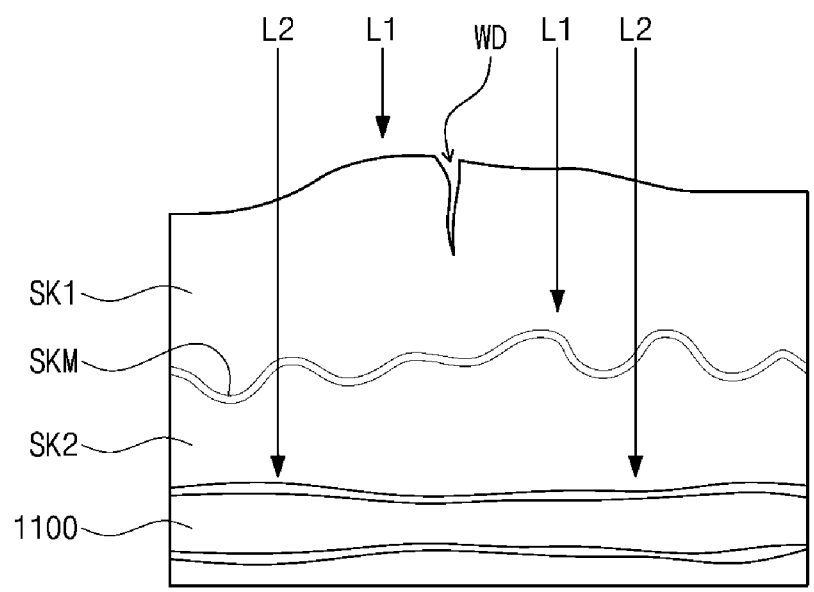
FIG. 5C illustrates an exemplary view of new cells generated in the wounded site shown FIG. 5B.

Referring to FIGS. 4 and 5C, new cells are generated in the wounded site where the pathogens are removed by the first light L1 and the second light L2, and the wounded site is gradually reduced.

Figure 5D:
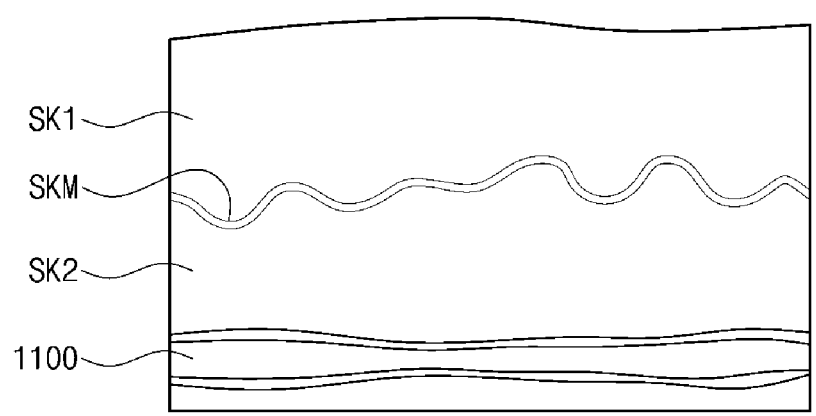
FIG. 5D illustrates an exemplary view of a cured wounded site.

As shown in FIGS. 4 and 5D, as the wounded site may be regenerated and healed, the wound may be completely cured, and the expanded blood vessel 1100 contracts again.

Figure 6A:
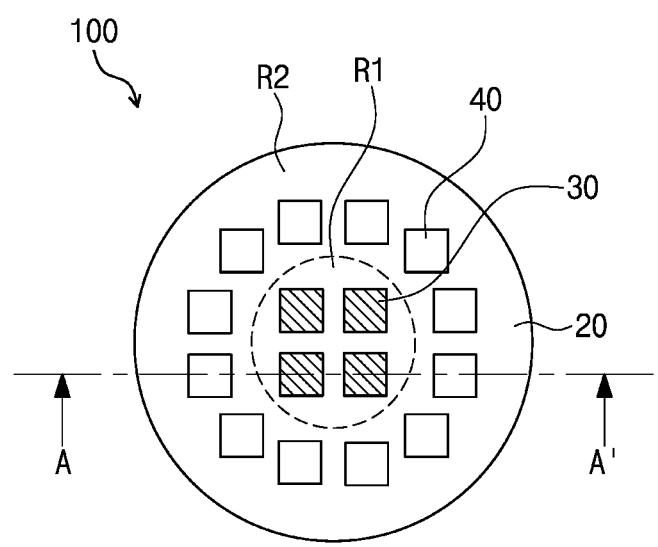
FIG. 6A is a plan view showing a light irradiation device according to an exemplary embodiment of the present disclosure.

The light irradiation device 100 according to the exemplary embodiment of the present disclosure may be implemented in various forms for the treatment of the skin. FIG. 6A is a plan view showing a light irradiation device 100 according to an exemplary embodiment of the present disclosure, and FIG. 6B is a cross-sectional view taken along a line A-A' of FIG. 6A.

Figure 6B:
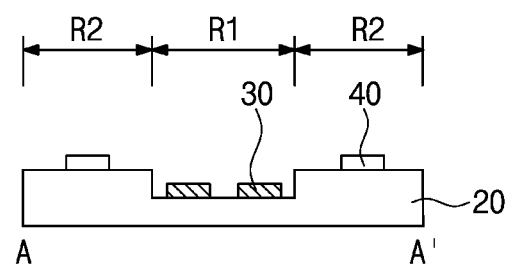
FIG. 6B is a cross-sectional view taken along a line A-A' of FIG. 6A.

Referring to FIGS. 6A and 6B, the light irradiation device 100 according to the exemplary embodiment of the present disclosure may include a first light source 30, a second light source 40, and a substrate 20 on which the first and second light sources 30 and 40 are mounted. More specifically, FIG. 6A illustrates a plan view of the light irradiation device 100 and FIG. 6B illustrates a cross sectional view of FIG. 6B.

In the present exemplary embodiment, the first light source 30 may be provided in a plural number, and the second light source 40 may also be provided in a plural number. However, the number of the first and second light sources 30 and 40 should not be particularly limited, and the number of the first light sources 30 may be greater than, smaller than, or equal to the number of the second light sources 40. In addition, according to the exemplary embodiment of the present disclosure, the first light sources 30 and the second light sources 40 may be regularly or irregularly arranged depending on the number of the first light sources 30 and the number of the second light sources 40.

In the exemplary embodiment of the present disclosure, the first and second light sources 30 and 40 may be arranged such that an area on the skin to which a first light from the first light sources 30 is provided and an area on the skin to which a second light from the second light sources 40 is provided are different from each other.

In some embodiments, since the first light is to sterilize pathogens penetrating through the wound, the sterilization may be sufficiently performed even though the first light is irradiated only in a relatively small area. The second light is to expand the blood vessel around the wound and to activate the immune mechanism, so that the second light needs to be irradiated to an area wider than the area where the wound is formed.

To this end, the second light sources 40 may be provided in large numbers so as to cover a relatively larger area than the first light sources 30, or may be arranged to have a wide light directivity angle. On the other hand, the first light sources 30 may be provided in relatively small numbers so as to cover a relatively smaller area than the second light sources 40 or may be arranged to have a narrow light directivity angle. As another way, depending on devices, additional components, such as a lens or a shade, for controlling a light irradiation area of the first light sources 30 and the second light sources 40 may be further disposed in the light irradiation device 100.

In the substrate 20 of the exemplary embodiment shown in FIGS. 6A and 6B, when an area in which the first light sources 30 are arranged, which faces the skin, is referred to as a "first region R1" and an area in which the second light sources 40 are arranged is referred to as a "second region R2", the second region R2 surrounds the first region R1. A surface corresponding to the first region R1 may be concaved from a surface corresponding to the second region R2, so that the first region R1 is more spaced apart from the skin than the second region R2 is. Accordingly, the second region R2 around the first light sources 30 arranged in the first region R1 has a protruding shape, and the light emitted from the first light sources 30 may be partially blocked by the protruding portion. Therefore, the light emitted from the first light sources 30 may travel in a direction that is not blocked by the protruding portion. As a result, the area of the skin to which the light emitted from the first light sources 30 is applied may be relatively reduced. Since the second light sources 40 are arranged in the portion that is more protruded than the first region R1, a periphery of the second light sources 40 is in a relatively open state, and thus, there is less limitation in the traveling direction of the light emitted from the second light sources. Thus, the second light may be applied to the area of the skin, which is relatively wider than the area of the skin to which the first light is applied.

In the exemplary embodiment of the present disclosure, the substrate 20 on which the first and second light sources 30 and 40 are mounted includes the first region R1 and the second region R2 and has the shape varying depending on the first region R1 and the second region R2. The shape of the substrate 20 should not be limited thereto or thereby. For example, the substrate 20 may have a flat shape in other embodiments. It should not be particular limited, and arrangements of the first and second light sources 30 and 40 and the substrate 20 may be changed depending on separate components, for example, a separate support member. For example, the substrate 20 may be disposed on a flat support member without a step difference, and the first and second light sources 30 and 40 may be disposed on the substrate 20. Alternatively, the substrate 20 may be disposed on a support member having a stepped portion, and the first and second light sources 30 and 40 may be disposed on the substrate 20. Further, one substrate 20 is provided in the present exemplary embodiment, however, the substrate 20 may be provided in a plural number, i.e., one or more substrates may be provided.

Although not shown in figures, the light irradiation device 100 according to the exemplary embodiment of the present disclosure may further include a housing that accommodates the first and second light sources 30 and 40 and the substrate 20. The housing may be provided with a transmission window through which the lights emitted from the first and second light sources 30 and 40 pass, the lights emitted from the first and second light sources 30 and 40 may be provided to the human body after passing through the transmission window.

In the exemplary embodiment of the present disclosure, a controller may be disposed on the substrate 20 in various ways. For instance, the controller may be formed on the substrate 20 as separate circuit wirings or may be mounted on the substrate 20 after being formed in a separate chip.

Figure 7A:
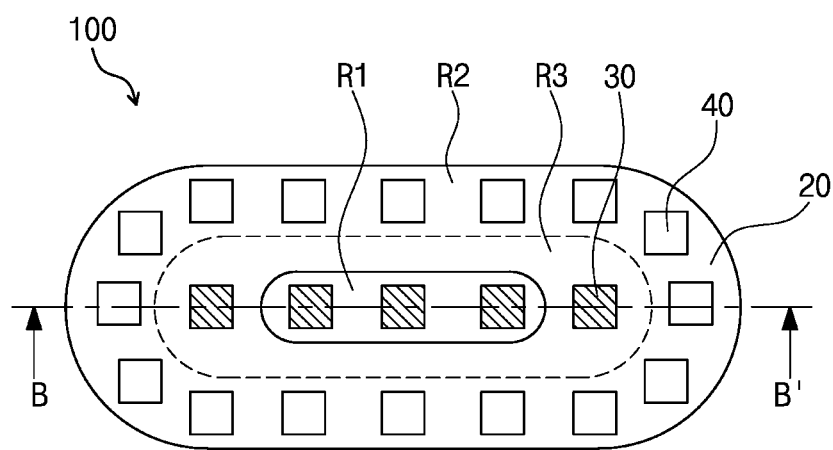
FIG. 7A is a plan view showing a light irradiation device according to an exemplary embodiment of the present disclosure.

The light irradiation device according to an exemplary embodiment of the present disclosure may be implemented in various forms. FIG. 7A is a plan view showing a light irradiation device 100 according to an exemplary embodiment of the present disclosure, and FIG. 7B is a cross-sectional view taken along a line B-B' of FIG. 7A.

Figure 7B:
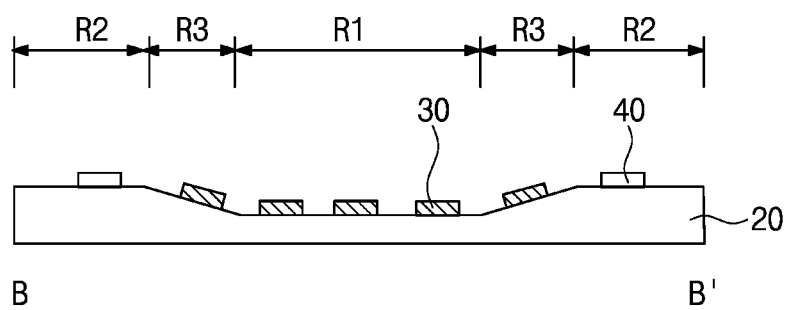
FIG. 7B is a cross-sectional view taken along a line B-B' of FIG. 7A.

Referring to FIGS. 7A and 7B, in the light irradiation device 100 according to the exemplary embodiment of the present disclosure, a shape or size of an area to which the light is provided may be set differently depending on a shape or condition of the skin or wound. For example, in the present exemplary embodiment, the light irradiation device 100 extends in a direction (direction B-B' in FIGS. 7A and 7B). This light irradiation device 100 may be used for a portion elongated in one direction, such as an arm, or when the wound itself is formed long.

In the present exemplary embodiment, the substrate 20 may include a first region R1 disposed at a center portion and corresponding to a concave portion, a second region R2 surrounding the first region R1 and corresponding to a convex portion, and a third region R3 disposed between the first region R1 and the second region R2 and corresponding to an inclined portion. The inclination of the third region R3 is formed inwardly, that is, in a direction toward the center portion.

First light sources 30 may be arranged in the first and third regions R1 and R3, and second light sources 40 may be arranged in the second region R2. Since the first light sources 30 are arranged in the concave portion or the portion inclined inwardly, the area of the skin to which the light emitted from the first light sources 30 is applied may be relatively reduced. Since the second light sources 40 are arranged in the portion that is more protruded than the first region R1, a periphery of the second light sources 40 is in a relatively open state, and thus, there is less limitation in the traveling direction of the light emitted from the second light sources 40. Thus, the second light may be applied to the area of the skin, which is relatively wider than the area of the skin to which the first light is applied.

In the embodiments described above, the light irradiation device may be implemented in various forms and used for various purposes. For example, the light irradiation device according to the exemplary embodiment of the present disclosure may be applied to various places where a lighting and a sterilization are necessary, and in particular, may be used as a lighting device. For example, the light irradiation device may be used for medical facilities, such as operating rooms and hospitals, lighting facilities for public health or personal hygiene. In particular, the light irradiation device according to the exemplary embodiment of the present disclosure may be used for the purpose of treating patients.

The light irradiation device according to the present disclosure may be applied to public facilities, public spaces, and shared products to be used for the purpose of public treatment, or may be applied to personal facilities, personal spaces, and personal use products to be used for the purpose of personal treatment. In addition, the light irradiation device according to the present disclosure may be used in addition to other treatment devices. That is, the light irradiation device according to the present disclosure may be additionally mounted to a variety of light treatment devices. Further, the light irradiation device according to the present disclosure may be used as a lighting device mounted on walls and a ceiling that form a predetermined space (e.g., a chamber).

Figure 8:
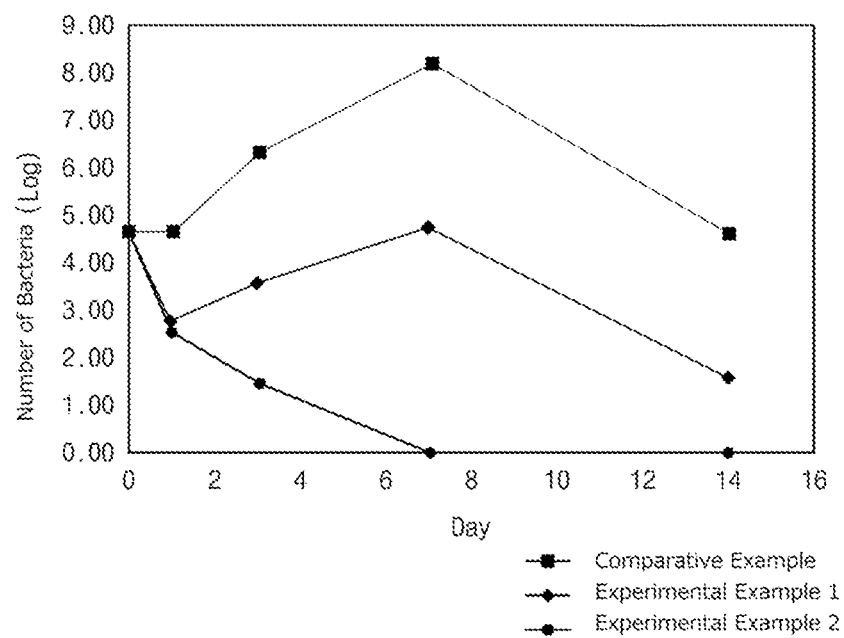
Figure 9:
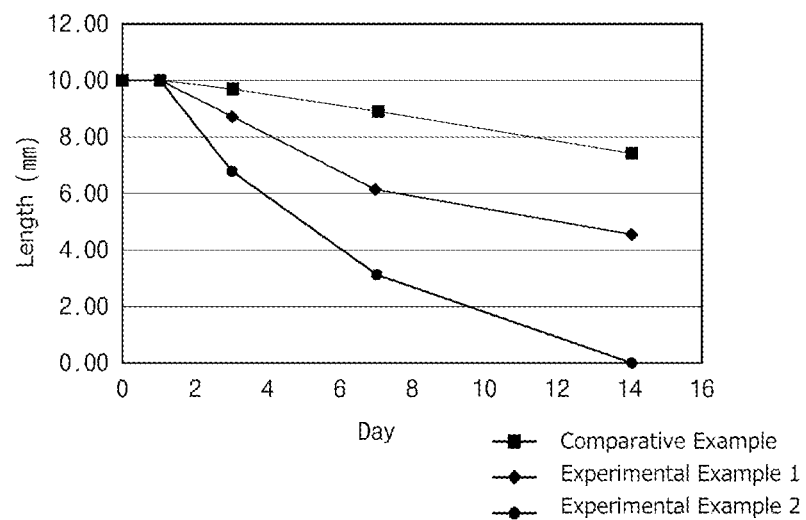

FIG. 8 is a graph showing sterilization effects in accordance with irradiation conditions when a light is irradiated to a wound using a conventional light irradiation device and a light irradiation device according to an exemplary embodiment of the present disclosure. FIG. 9 is a graph showing a recovery period of the wound in accordance with the irradiation conditions when the light is irradiated to the wound using a conventional light irradiation device and a light irradiation device according to an exemplary embodiment of the present disclosure.

In FIG. 8, a comparative example indicates a state in which none of the first light and the second light is irradiated, an experimental example 1 indicates a state in which the ultraviolet light is irradiated using a sterilizing ultraviolet light irradiation device, and an experimental example 2 indicates a state in which the first light and the second light are irradiated using the light irradiation device according to the exemplary embodiment of the present disclosure.

For the comparative example, the experimental example 1, and the experimental example 2, a hair on the back of a laboratory mouse was removed, and a 10-mm wound was produced in a 10 mm by 100 mm area on the back of the mouse using a sharp blade. In this case, the wound was induced by scratching the dermis layer and causing the laboratory rat to bleed from the back. Then, a pathogenic bacterium, e.g., Methicillin-resistant *Staphylococcus aureus* (MRSA), was inoculated as a pathogen. Tissues of the wound were collected on the specified dates to check the number of bacteria and measure the length of the wound. The light used in experimental example 1 was the ultraviolet light, a wavelength of the ultraviolet light was about 254 nm, and a dose of the ultraviolet light was about 150 mJ/cm². A wavelength of the first light used in the experimental example 2 was about 410 nm, and a dose of the first light was about 120 J/cm². A wavelength of the second light used in the experimental example 2 was about 850 nm, and a dose of the second light was about 60 J/cm². The lights of experimental example 1 and experimental example 2 were irradiated three times in total for three consecutive days. Table 2 shows the sterilization effect depending on irradiation conditions as the number of bacteria when the light is irradiated to the wound using a conventional light irradiation device and the light irradiation device according to the exemplary embodiment of the present disclosure, and the number of bacteria is presented on a log scale.

TABLE 2

| Date (days) | Comparative example | Experimental example 1 | Experimental example 2 |
| --- | --- | --- | --- |
| 0 (the day of inoculation) | 4.62 | 4.62 | 4.62 |
| 1 | 4.62 | 2.78 | 2.56 |
| 3 | 6.27 | 3.56 | 1.47 |
| 7 | 8.18 | 4.75 | 0.00 |
| 14 | 4.62 | 1.56 | 0.00 |

Referring to Table 2 and FIG. 8, in the comparative example in which none of the lights is irradiated, the number of bacteria did not decrease even after 14 days had passed, but rather, the number of bacteria increased in the middle of the process. In particular, after the wound was infected with bacteria, the number of bacteria continued to increase from day 1 to day 7, and after more time elapsed, the number of bacteria decreased. The reason why the number of bacteria increased gradually from day 1 to day 7 was thought to be caused by the result of the growth of bacteria in the wound and the wounded site without being terminated. Since then, some of the bacteria were killed by the immune response, and thus, the number of bacteria seemed to have decreased.

In Experimental example 1, it was observed that the number of bacteria was decreased on day 1 by applying the ultraviolet light to the wound. It seemed that the ultraviolet light had the sterilization effect on the skin. However, it was observed that the number of bacteria increased from day 3 to day 7 after day 1. This is because some of the bacteria in the epidermis close to the surface of the skin were killed by the ultraviolet light, but bacteria located at an inner portion of the epidermis and in the dermis remain without being terminated and then re-proliferate when the skin is sterilized by using the ultraviolet light. Since the ultraviolet light has a very small penetration depth in the skin, it is difficult to thoroughly kill bacteria located at the inner portion the epidermis and in the dermis.

In Experimental example 2, the number of the bacteria was gradually decreased as time went on. This is interpreted as the case where the sterilization of bacteria in the epidermis by the first light is substantially performed with the sterilization of bacteria at the inner portion of the epidermis and in the dermis by the promotion of immune response.

Table 3 shows the recovery period of the wound depending on irradiation conditions when the light is irradiated to the wound using a conventional light irradiation device and the light irradiation device according to the exemplary embodiment of the present disclosure, and the length of the wound as a function of the elapse of time is shown.

TABLE 3

| Date (days) | Comparative example | Experimental example 1 | Experimental example 2 |
| --- | --- | --- | --- |
| 0 (the day of inoculation) | 10.00 | 10.00 | 10.00 |
| 1 | 10.00 | 10.00 | 10.00 |
| 3 | 9.73 | 8.83 | 6.93 |
| 7 | 8.98 | 6.26 | 3.37 |
| 14 | 7.50 | 4.79 | 0.00 |

Referring to Table 3 and FIG. 9, in Comparative example in which none of the lights is irradiated, the recovery of the wound was very slow even after 14 days had passed.

In Experimental example 1, the recovery of the wound was faster than the comparative example; however, the recovery of the wound is still slow, and only about 50% of the wound was recovered on the 14th day.

In Experimental example 2, the recovery of the wound was very faster than the comparative example and experimental example 1. On the 14th day, the wound was 0 mm in length, and the wound was healed completely. In experimental example 2, it was observed that immune response and skin regeneration response by the improvement in blood flow were promoted in addition to sterilization.

As described above, the light irradiation device according to the exemplary embodiment of the present disclosure may effectively sterilize the wound and may significantly reduce the recovery period of the wound.

Although the exemplary embodiments of the present disclosure have been described, it is understood that the present disclosure should not be limited to these exemplary embodiments but various changes and modifications can be made by one ordinary skilled in the art within the spirit and scope of the present disclosure as hereinafter claimed.

Therefore, the disclosed subject matter should not be limited to any single embodiment described herein, and the scope of the present inventive concept shall be determined according to the attached claims.

The invention claimed is:

1. A light irradiation device, comprising:
a light source unit emitting a light to a skin area to be treated; and
a controller operable to control the light source unit;
the light source unit comprising:
a substrate:
   first light sources disposed on the substrate and emitting a first light in a blue wavelength band; and
   second light sources disposed on the substrate and emitting a second light in a red wavelength band to a near-infrared wavelength band, wherein the first light has a first skin penetration depth and the second light has a second skin penetration depth, the first skin penetration depth and the second skin penetration depth differing depending on a wavelength and the first skin penetration depth being smaller than the second skin penetration depth;
wherein a first group of first light sources is disposed in a first region corresponding to a first portion of a surface of the substrate, and a group of the second light sources is disposed in a second region surrounding the first region and corresponding to a second portion of the surface of the substrate, wherein the first portion of the surface of the substrate is disposed at a center portion of the substrate and concaved relative to the second portion of the surface of the substrate such that the first group of first light sources is disposed on the first portion concaved from the second portion and the first group of second light sources is disposed on the second portion protruding from the first portion;
wherein a second group of first light sources is disposed in a third region located between the first region and the second region and corresponding to a third portion of the surface of the substrate and wherein the first portion, the third portion, and the second portion are sequentially arranged in a direction away from the center portion of the substrate such that all of second light sources in the group of second light sources are disposed along an edge of the substrate and located in the second region entirely surrounding the third region;
the first region is spaced apart from the skin area to be treated farther than the second region is;
wherein in the first region, direct application of the first light with a first predetermined dose, to the skin area to be treated, causes the first light to penetrate through the skin area to be treated and reactive oxygen species (ROS) to be produced and accumulated in cells of bacteria within the first skin penetration depth, thereby resulting in demise of the bacteria;
in the second region, direct application of the second light with a second predetermined dose, to an area wider than the skin area to be treated by the first light and in an open state, causes the second light to penetrate through the skin area to be treated and blood vessels to be dilated and promote a blood circulation in the second skin penetration depth, thereby improving a blood flow and promoting immune response,
wherein the third portion of the surface has an inclined surface connecting the first region and the second region.

2. The light irradiation device of claim 1, wherein the first light has the first skin penetration depth equal to or greater than about 1.0 mm.

3. The light irradiation device of claim 2, wherein the second light has the second skin penetration depth equal to or greater than about 4.3 mm.

4. The light irradiation device of claim 1, wherein the first light has a wavelength band of about 370 nm to about 500 nm.

5. The light irradiation device of claim 4, wherein the first light has a wavelength band of about 385 nm to about 435 nm.

6. The light irradiation device of claim 4. wherein the second light has a wavelength band of about 610 nm to about 940 nm.

7. The light irradiation device of claim 1, wherein both the first light and the second light are irradiated for a predetermined time period.

8. The light irradiation device of claim 1, wherein the first light is irradiated for a first time, and the second light is irradiated for a second time longer than the first time.

9. The light irradiation device of claim 8, wherein the second light starts to be irradiated before the irradiation of the first light is completed, and at least a portion of the first time overlaps with at least a portion of the second time.

10. The light irradiation device of claim 9, wherein the second light is irradiated continuously.

11. The light irradiation device of claim 7, wherein the first light is irradiated at intervals and the first light is discontinuous.

12. The light irradiation device of claim 7, wherein the first light, the second light, or both are periodically irradiated.

13. The light irradiation device of claim 1, wherein the light irradiation device is for treatment; and
wherein the substrate faces the skin area to be treated and comprises the first region and the second region; and
the first region and the second region are concentrically arranged such that the second region surrounds the first region.

14. The light irradiation device of claim 1, wherein an irradiation area of the first light on the skin area to be treated is smaller than an irradiation area of the second light on the skin.

15. The light irradiation device of claim 1, wherein the second predetermined dose is about a half of the first predetermined dose.

16. A light irradiation device comprising:
first light sources emitting a first light in a blue wavelength band;
second light sources emitting a second light in a red wavelength band to a near-infrared wavelength band; and
a controller configured to control the first and second light sources,
wherein the first light has a first skin penetration depth and the second light has a second skin penetration depth, the first skin penetration depth and the second skin penetration depth differing depending on a wavelength;
the first skin penetration depth being smaller than the second skin penetration depth;
wherein a first group of first light sources is disposed in a first region corresponding to a first portion of a surface of a substrate, a group of the second light sources is disposed in a second region surrounding the first region and corresponding to a second portion of the surface of the substrate, wherein the first portion of the surface of the substrate is disposed at a center portion of the substrate and concaved relative to the second portion of the surface of the substrate such that the first group of first light sources is disposed on the first portion concaved from the second portion and the first group of second light sources is disposed on the second portion protruding from the first portion;
wherein a second group of first light sources is disposed in a third region located between the first region and the second region and corresponding to a third portion of the surface of the substrate and wherein the first portion, the third portion, and the second portion are sequentially arranged in a direction away from the center portion of the substrate such that all of second light sources in the group of second light sources are disposed along an edge of the substrate and located in the second region entirely surrounding the third region;
the first region is spaced apart from a skin area to be treated farther than the second region is;
wherein in the first region, a direct application of the first light with a first predetermined dose, to a skin area to be treated, causes the first light to penetrate through the skin area to be treated and reactive oxygen species (ROS) to be produced and accumulated in cells of bacteria within the first skin penetration depth, thereby resulting in demise of the bacteria;
in the second region, direct application of the second light with a second predetermined dose, to an area wider than the skin area to be treated by the first light and in an open state, causes the second light to penetrate through the skin area to be treated and blood vessels to be dilated and promote a blood circulation in the second skin penetration depth, thereby improving a blood flow and promoting immune response,
wherein the third portion of the surface has an inclined surface connecting the first region and the second region.

17. The light irradiation device of claim 16, wherein the first light has the skin penetration depth equal to or greater than about 0.8 mm, and the second light has the skin penetration depth equal to or greater than about 4.3 mm;
wherein the substrate faces a skin area to be treated and comprises a first region in which the first light source is disposed and a second region in which the second light source is disposed; and
the first region and the second region concentrically arranged.

18. The light irradiation device of claim 17, wherein the first light has a wavelength band of about 370 nm to about 500 nm.

19. The light irradiation device of claim 16, wherein the first light is irradiated for a first time, and the second light is irradiated for a second time longer than the first time; and
the second light starts to be irradiated before the irradiation of the first light is completed, and at least a portion of the first time overlaps with at least a portion of the second time.

20. The light irradiation device of claim 16, wherein the second predetermined dose is about a half of the first predetermined dose.

* * * * *